July 7, 1964 E. S. BOERNER Plant Pat. 2,421
ROSE PLANT
Filed Aug. 26, 1963
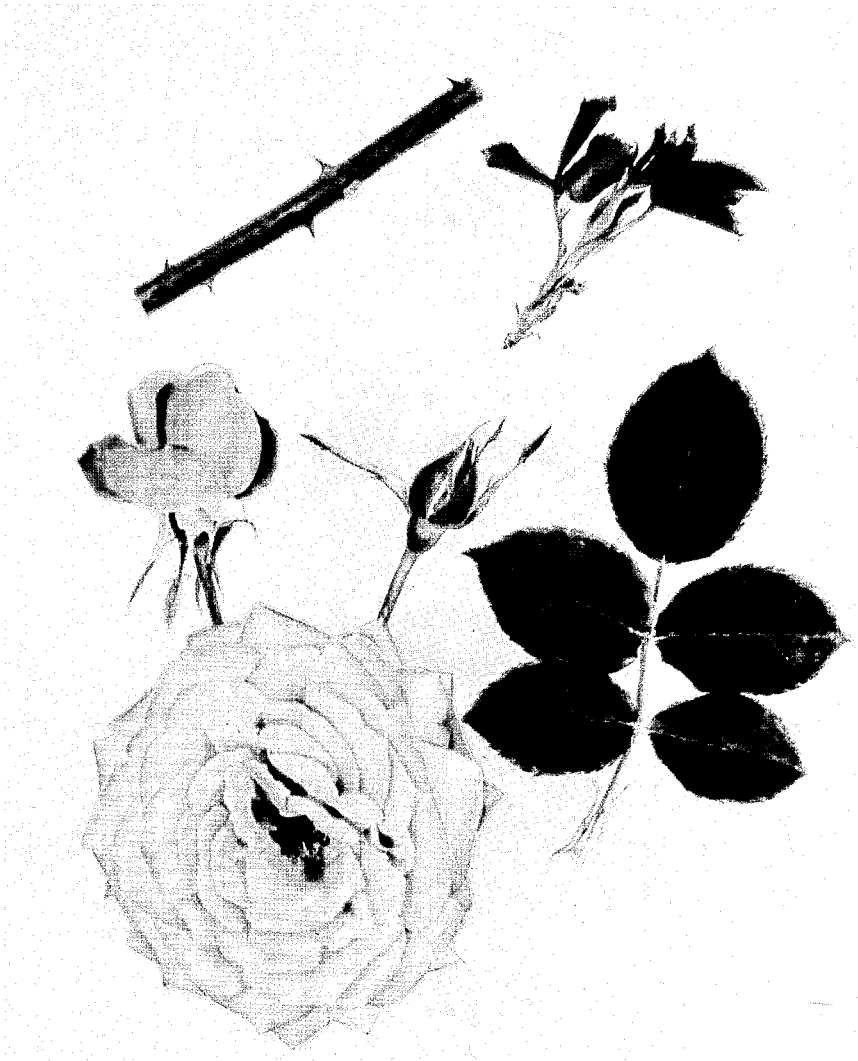
Inventor.
E. S. Boerner
By: Robb & Robb
Attorneys.

United States Patent Office

Plant Pat. 2,421
Patented July 7, 1964

2,421
ROSE PLANT

Eugene S. Boerner, Newark, N.Y., assignor to Jackson & Perkins Company, Newark, N.Y., a corporation of New York Filed Aug. 26, 1963, Ser. No. 304,706
1 Claim. (Cl. Plt.—11)

The present invention relates to a new and distinct variety of rose plant of the hybrid tea class, which was originated by me by crossing the variety "Brownie" (Plant Patent No. 1,720) with the variety "Sterling Silver" (Plant Patent No. 1,433).

The primary objective of this breeding was to produce a new rose variety which is large-flowered, free-flowering and bears flowers of lavender color. This objective was fully achieved, along with other desirable features, as evidenced by the following unique combination of characteristics which are outstanding in the new variety and which distinguish it from its parents, as well as from all other varieties of which I am aware:

(1) A free-flowering habit resulting in a profusion of flowers on each plant;

(2) A large, double and cupped flower form;

(3) A distinctive and attractive general color tonality of the flowers corresponding to Persian Lilac, very lightly overcast with Pale Persian Lilac; and (4) A rich centifolia flower fragrance.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Brownie."
*Pollen parent.*—"Sterling Silver."
Classification:
*Botanic.*—Hybrid tea.
*Commercial.*—Hybrid tea.

*Flower*

(Observations made from specimens grown outdoors at Newark, New York, in the early morning during the eary part of the month of September.)

Blooming habit: Recurrent—continuous; free-flowering.
Bud:
*Size.*—Large.
*Form.*—Ovoid; is not affected by wet or hot weather.
*Color.*—When sepals first divide—Schoenfeld's Purple, Plate 26. When petals begin to unfurl—Deep Hellebore Red, Plate 38. When half-blown: inside of petals—Hellebore Red, Plate 38; reverse of petals—Laelia Pink, Plate 38, very lightly overcast with Hellebore Red, Plate 38.
*Sepals.*—Smooth edge; curl back when petals begin to unfurl. Color: inside—Light Mineral Gray, Plate 47; outside—Chromium Green, Plate 32, with upper half of sepal lightly overcast with Dahlia Carmine, Plate 26.

*Calyx.*—Color—Light Bice Green, Plate 17. Shape—pear. Size—small. Aspect—smooth. Odor when rubbed—none.
*Peduncle.* — Length — medium. Aspect — rough. Strength—erect; slender. Color—Light Cress Green, Plate 31, lightly overcast with Dark Citrine, Plate 4.
*Opening.*—Opens up well; is not affected by adverse weather conditions.
Bloom:
*Size.*—Large. Average size when fully expanded—from 4½ inches to 5 inches.
*Borne.*—Both singly and several together; great profusion of flowers on each plant.
*Stems.*—Medium length; strong.
*Form (when first open).*—Cupped. Permanence—retains its form to the end.
*Petalage.*—Double (full but open center). Number of petals under normal conditions—from 45 to 50.
*Color.*—Center of flower—Rhodonite Pink, Plate 38, lightly overcast with Hellebore Red, Plate 38. Outer petals—Pale Persian Lilac, Plate 38, lightly overcast with Persian Lilac, Plate 38. Base of petals (aiglet)—Citron Yellow, Plate 16. Inside of petals—Persian Lilac, Plate 38, very lightly overcast with Pale Persian Lilac, Plate 38. Reverse of petals—Pale Vinaceous Lilac, Plate 44, very lightly overcast with Pale Persian Lilac, Plate 38. General tonality from a distance—Persian Lilac, Plate 38, lightly overcast with Pale Persian Lilac, Plate 38.
*Discoloration.*—General tonality at end of first day—Persian Lilac Plate 38. Second day—Persian Lilac, Plate 38. Third day—Persian Lilac, Plate 38, overcast with Pale Persian Lilac, Plate 38.
Petals:
*Texture.*—Leathery; is not affected by wet or hot weather.
*Appearance.*—Inside—satiny. Outside—shiny.
*Form.*—Oval pointed.
*Arrangement.*—Imbricated (regularly arranged shingle-like).
*Petaloids in center.*—Few; large.
*Persistence.*—Drop off cleanly.
*Fragrance.*—Strong. Nature—"Old Rose perfume" (centifolia).
*Lasting quality.*—On plant—long. As cut flower—long.

*Genital Organs*

Stamens, anthers: Medium size; many regularly arranged around styles. Color—Buff Yellow, Plate 4.
Stamens, filaments (threads): Medium length. Color—Pinard Yellow, Plate 4.
Pollen: Color—Baryta Yellow, Plate 4.
Styles: Bunched; uneven length; medium length; thin.
Stigmas: Color—Picric Yellow, Plate 4.
Ovaries: All enclosed in calyx.
Hips: None.
Seeds: None.

*Plant*

Form: Bush.
Growth: Vigorous; upright; bushy.
Foliage: Compound of 5–7 leaflets.
*Size.*—Medium.
*Quantity.*—Normal.
*Color.*—New foliage: upper side—Lettuce Green, Plate 5, with outer edges overcast with Van Dyke Red, Plate 1; under side—Oxblood Red, Plate 1, with center of leaf Yellowish Citrine, Plate 16. Old foliage: upper side—Forest Green, Plate 17;

under side—Courge Green, Plate 17.

*Shape.*—Oval pointed.

*Texture.*—Upper side—leathery. Under side—smooth.

*Ribs and veins.*—Ordinary.

*Edge.*—Serrated (saw-toothed).

*Serration.*—Both double and single; small.

*Leaf stem.*—Color—Light Bice Green, Plate 17. Under side—smooth.

*Stipules.*—Medium length; bearded.

Wood:

*New wood.*—Color—Deep Chrysolite Green, Plate 31. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form—narrow base: medium length; hooked downward.

Color (when young)—Eugenia Red, Plate 13. Position—irregular.

*Prickles.*—Quantity: on main stalks—few; on laterals—few.

*Short needles.*—Quantity: on main stalks—none; on laterals—none.

I claim:

A new and distinct variety of rose plant of the hybrid tea class, substantially as herein shown and described, characterized particularly as to novelty by the unique combination of a free-flowing habit, with consequent profusion of flowers on each plant, a large, double and cupped flower form, a distinctive and attractive general color tonality of the flowers corresponding to Persian Lilac, very lightly overcast with Pale Persian Lilac, and a rich centifolia flower fragrance.

No references cited.